United States Patent
Hazel et al.

(10) Patent No.: US 10,512,902 B2
(45) Date of Patent: Dec. 24, 2019

(54) CARBONYLATION PROCESS USING A PRETREATED ZEOLITE CATALYST

(71) Applicant: BP Chemicals Limited, Sunbury-on-Thames, Middlesex (GB)

(72) Inventors: Nicholas John Hazel, Beverley (GB); David John Law, Hull (GB)

(73) Assignee: BP Chemicals Limited, Middlesex (GB)

( * ) Notice: Subject to any disclaimer, the term of this patent is extended or adjusted under 35 U.S.C. 154(b) by 0 days.

(21) Appl. No.: 16/063,647

(22) PCT Filed: Nov. 25, 2016

(86) PCT No.: PCT/EP2016/078776
§ 371 (c)(1),
(2) Date: Jun. 18, 2018

(87) PCT Pub. No.: WO2017/102284
PCT Pub. Date: Jun. 22, 2017

(65) Prior Publication Data
US 2018/0369794 A1   Dec. 27, 2018

(30) Foreign Application Priority Data
Dec. 18, 2015 (EP) .................................... 15201113

(51) Int. Cl.
| | |
|---|---|
| *B01J 29/18* | (2006.01) |
| *B01J 38/06* | (2006.01) |
| *B01J 29/50* | (2006.01) |
| *B01J 29/65* | (2006.01) |
| *B01J 29/70* | (2006.01) |
| *C07C 67/37* | (2006.01) |
| *C07C 69/12* | (2006.01) |
| *B01J 38/04* | (2006.01) |
| *B01J 29/90* | (2006.01) |

(52) U.S. Cl.
CPC ............... *B01J 29/18* (2013.01); *B01J 29/50* (2013.01); *B01J 29/65* (2013.01); *B01J 29/70* (2013.01); *B01J 38/06* (2013.01); *C07C 67/37* (2013.01); *C07C 69/12* (2013.01); *B01J 29/90* (2013.01); *B01J 38/04* (2013.01); *B01J 2229/24* (2013.01); *B01J 2229/34* (2013.01); *B01J 2229/36* (2013.01); *B01J 2229/42* (2013.01); *Y02P 20/584* (2015.11)

(58) Field of Classification Search
CPC ................................. B01J 29/18; B01J 29/50; C07C 67/37; C07C 69/12
USPC .......................................................... 560/232
See application file for complete search history.

(56) References Cited

U.S. PATENT DOCUMENTS

| | | |
|---|---|---|
| 2006/0252633 A1 | 11/2006 | Ghosh et al. |
| 2008/0249327 A1 | 10/2008 | Eckelt et al. |
| 2011/0313224 A1 | 12/2011 | Chewter et al. |

FOREIGN PATENT DOCUMENTS

| | | | |
|---|---|---|---|
| WO | WO-2014111508 A | * 7/2010 | ............. B01J 29/18 |
| WO | WO 2014/111508 | 7/2014 | |

OTHER PUBLICATIONS

Huifu Xue et al.: "Selective dealunnination of mordenite for enhancing its stability in dimethyl ether carbonylation", Catalysis Communications, vol. 37, Jul. 1, 2013 (Jul. 1, 2013), pp. 75-79, (Year: 2013).*
International Search Report and Written Opinion for International Application No. PCT/3P2016/079776 dated Feb. 10, 2017, 13 pages.
Huifu Xue et al. "Selective dealumination of mordenite for enhancing its stability in dimethyl ether carbonylation," Catalysis Communications 37:75-79 (2013).

* cited by examiner

*Primary Examiner* — Deborah D Carr
(74) *Attorney, Agent, or Firm* — McDonnell Boehnen Hulbert & Berghoff LLP

(57) ABSTRACT

A carbonylation process in the presence of a pretreated zeolite catalyst which comprises the sequential steps (i) pretreating the catalyst and (ii) carbonylating dimethyl ether with a carbon monoxide-containing gas to produce methyl acetate in which the catalyst pretreatment step (i) comprises a step (a) contacting the catalyst with a first treatment mixture comprising water vapour; and a step (b) contacting the treated catalyst of step (a) with a second treatment mixture comprising an inert gas and at least one of dimethyl ether and methanol.

18 Claims, No Drawings

CARBONYLATION PROCESS USING A PRETREATED ZEOLITE CATALYST

This application is a national stage application under 35 U.S.C. § 371 of International Application No. PCT/EP2016/078776, filed Nov. 25, 2016, which claims priority to EP Patent Application No. 15201113.6, filed Dec. 18, 2015, the disclosures of which are explicitly incorporated by reference herein.

Methyl acetate is used industrially in petrochemical processes, particularly as a feedstock for the production of commodity chemicals such as acetic acid and acetic anhydride.

Crystalline aluminosilicate zeolites have been found to catalyse the carbonylation of dimethyl ether to produce methyl acetate. For example, WO 2006/121778 describes a process for the production of a lower aliphatic ester of a lower aliphatic carboxylic acid by carbonylating lower alkyl ethers with carbon monoxide in the presence of a mordenite or ferrierite catalyst under substantially anhydrous conditions.

In U.S. Pat. No. 7,465,822 it is demonstrated that zeolites for the carbonylation of dimethyl ether to produce methyl acetate contain at least one 8-member ring channel such as those of framework type MOR, FER, OFF and GME. By contrast, zeolites not containing 8-member ring channels, such as ZSM-5 (framework type MFI), were shown to provide poor catalytic performance for this reaction.

An important aspect of any catalytic process is the performance of a catalyst when exposed to normal process conditions. The improvement of catalytic performance in carbonylation reactions is a continuous objective of process and catalyst development.

A disadvantage associated with the use of zeolites as catalysts for carbonylation processes is that they deactivate over time with a commensurate decrease in the production rate of carbonylation products. Without being bound by theory, it is believed that the deactivation of zeolite catalysts in processes for the carbonylation of dimethyl ether may be attributable to side reactions of dimethyl ether or the methyl acetate product leading to the formation of hydro carbonaceous (coke) deposits on the catalyst surface. These deposits restrict access to catalytic active sites and eventually the production rate of carbonylation products is sufficiently reduced as to necessitate replacement or regeneration of the catalyst.

Processes for regenerating zeolite catalysts for use in carbonylation processes are known from, for example WO 2009/077745 and WO 2009/077739.

WO 2009/077745 describes a process for the in-situ regeneration of a mordenite catalyst in the carbonylation of a carbonylatable reactant such as dimethyl ether to form methyl acetate, in which the catalyst is regenerated by contacting the catalyst with a regenerating gas comprising a molecular oxygen-containing gas and an inert diluent at a total pressure in the range 1 to 100 bar and at an molecular oxygen-containing gas partial pressure such that the temperature of the catalyst is maintained within the range 225° C. to 325° C.

WO 2009/077739 describes a process for the in-situ regeneration of a zeolite catalyst for the production of methyl acetate by contacting a carbonylatable reactant such as dimethyl ether with carbon monoxide in the presence of the catalyst, ceasing contact of the catalyst with the carbonylatable reactant, regenerating the catalyst with a regenerating gas selected from hydrogen and a mixture of hydrogen and carbon monoxide at a temperature in the range 250 to 600° C., terminating the hydrogen regenerating step and resuming contact of the catalyst with the carbonylatable reactant and carbon monoxide.

However, one disadvantage associated with regeneration processes can be the time taken to perform the regeneration, particularly if undertaken in situ.

The process disclosed in WO 2014/111508 seeks to improve reduced catalytic performance of zeolite catalysts in carbonylation processes caused by or associated with coking of the catalyst by pretreating it with water vapour prior to its use in the carbonylation process.

Huifu Xue et al in 'Selective dealumination of mordenite for enhancing its stability in dimethyl ether carbonylation' Catalysis Communications 37 (2013) 75-79 carry out selective dealumination of the 12-MR channels of mordenite by steam treatment at 1023K in order to enhance catalyst stability in the carbonylation reaction.

As with any chemical process, it is desirable to develop new and improved catalysts. Applicant has now found that by pretreating a zeolite carbonylation catalyst with water vapour and additionally with a mixture of an inert gas and at least one of dimethyl ether and methanol uncontrolled coking of the catalyst is mitigated leading to reduced heat generation and improved catalytic performance in processes for the carbonylation of dimethyl ether with a carbon monoxide-containing gas to produce a carbonylation reaction product comprising methyl acetate.

Accordingly, the present invention provides a process for the carbonylation of dimethyl ether with a carbon monoxide-containing gas in the presence of a zeolite carbonylation catalyst which process comprises the sequential steps of:
(i) pretreating the catalyst; and
(ii) carbonylating the dimethyl ether with the carbon monoxide-containing gas to produce a reaction product comprising methyl acetate;
wherein the pretreatment of the catalyst in step (i) comprises the steps:
   (a) contacting the catalyst with a first treatment mixture comprising water vapour; and
   (b) contacting the catalyst treated in step (a) with a second treatment mixture comprising an inert gas and at least one of dimethyl ether and methanol.

By 'inert gas' is meant any gas which does not react which dimethyl ether or methanol during pretreatment step (b) and thus, gases such as carbon monoxide, hydrogen, ethylene and ammonia are not considered to be inert gases for the purposes of the present invention. Suitable inert gases include nitrogen, helium, argon, carbon dioxide, methane and ethane.

In some or all embodiments of the present invention, the first treatment mixture is a mixture of water vapour and an inert gas and the inert gas component of the first and second treatment mixtures is the same or different.

In some or all embodiments of the present invention the first treatment mixture is a mixture of water vapour and an inert gas and the inert gas component of the first treatment mixture and the second treatment mixture is the same, which inert, gas is suitably nitrogen.

In some or all embodiments of the present invention the first treatment mixture is water vapour or a mixture of water vapour and an inert gas and the second treatment mixture is a mixture of water vapour, an inert gas and at least one of dimethyl ether and methanol. In these embodiments, the inert gas is suitably nitrogen.

In some or all embodiments of the present invention, the catalyst to be treated is a zeolite which has at least one channel which is defined by an 8-membered ring, for example a zeolite of framework type MOR, FER, OFF and GME, such as mordenite.

In some or all embodiments of the present invention, the catalyst pretreatment step (i) may be conducted in-situ, that is, in the same reaction vessel in which carbonylation step (ii) is to be carried out or ex-situ, that is, separately from the reaction vessel in which carbonylation step (ii) is to be carried out. Preferably pretreatment step (i) is conducted in-situ.

Dimethyl ether is a reaction component of carbonylation step (ii). Thus, suitably where dimethyl ether is a component of the second treatment mixture it forms all or a portion of the dimethyl ether feed to carbonylation step (ii). If desired, additional dimethyl ether, to that present in the second treatment mixture, may be introduced into carbonylation step (ii). Where dimethyl ether is not a component of the second treatment mixture, dimethyl ether is introduced as a feed in carbonylation step (ii). The carbon monoxide-containing gas, for example synthesis gas may be introduced together with or separately from the dimethyl ether feed to step (ii). Carbonylation reaction step (ii) is initiated by the reaction of dimethyl ether with a carbon monoxide-containing gas to produce a reaction product comprising methyl acetate.

Where methanol is a component of the second treatment mixture, it is discontinued prior to carbonylation step (ii) such that methanol is not a feed to the carbonylation process.

Without being bound by theory, it is believed that pretreating a zeolite carbonylation catalyst in accordance with the present invention results in a more controlled accumulation and distribution of coke on the surface of the zeolite during carbonylation processes and in particular, at start-up of the process. Applicant has found that this more controlled coking can reduce heat generation and decrease catalyst deactivation thereby allowing increased production rates (space time yields) to acetyls reaction products to be achieved.

The practical benefits of the present invention are numerous but include benefits such as carbonylation processes may now be operated for longer durations and at improved production rates before replacement or regeneration of the catalyst is required. Improved catalytic performance can result in reduced catalyst cost and/or a smaller carbonylation reactor resulting in lower capital expenditure.

Catalyst pretreatment step (i) of the present invention comprises a first step (a). In step (a), the catalyst is contacted with a first treatment mixture comprising water vapour.

Suitably, the partial pressure of water vapour in the first treatment mixture may be in the range 0.8 to 8 bar (80 to 800 kPa), for example 1 to 4.8 bar (100 to 480 kPa), preferably 3.2 to 4.8 bar (320 to 480 kPa).

The amount of water vapour in the first treatment mixture can vary depending on the desired carbonylation reaction pressure. Suitably, for reaction pressures in the range 50 to 100 barg (5000 to 10,000 kPa), water vapour is present in the first treatment mixture in an amount of 1 to 10 mol %, for example 4 to 6 mol %.

In some or all embodiments of the present invention, the first treatment mixture further comprises one or more inert gases, for example selected from nitrogen, helium, argon, carbon dioxide, methane and ethane, preferably nitrogen.

In some or all embodiments of the present invention, the first treatment mixture is a mixture of water vapour, suitably at a partial pressure in the range 0.8 to 8 bar (80 to 800 kPa) and one or more inert gases, for example selected from nitrogen, helium, argon and carbon dioxide, preferably nitrogen.

In some or all embodiments of the present invention, the first treatment mixture is a mixture of one or more inert gases, preferably nitrogen, and water vapour in an amount of from 1 to 10 mol %, for example 4 to 6 mol % and suitably, the carbonylation reaction pressure in step (ii) is in the range 50 to 100 barg (5000 to 10,000 kPa).

Dealumination of zeolites is a well-known concept within the art and refers to the removal of aluminium from the crystalline framework of the zeolite thereby modifying its silica alumina molar ratio (SAR). Removal of aluminium from zeolite frameworks may be deduced by known techniques such as $^{27}$Al MAS NMR. Techniques for the dealumination of zeolites are numerous but can be effected by subjecting a zeolite to hydrothermal treatment at high temperature, such as 600° C. or higher. For the purposes of the present invention, it is preferred that step (a) is carried out at temperatures which avoid significant dealumination of the zeolite occurring. For zeolites of the MOR framework type, such as mordenite, step (a) can be effectively carried out at temperatures in the range 250° C. to 350° C., such as 260° C. to 300° C. or 260° C. to 310° C., for example in the range 270° C. to 290° C.

Suitably, step (a) is carried out at the carbonylation reaction pressure desired to be used. Thus, step (a) may be carried out at a total pressure of from 1 to 100 barg (100 to 10,000 kPa), for example 20 to 80 barg (2000 to 8000 kPa), such as 50 to 80 barg (5000 to 8000 kPa) or 50 to 100 barg (5000 to 10,000 kPa).

Desirably, step (a) is carried out at a temperature of from 250° C. to 350° C., such as 260° C. to 300° C., for example from 270° C. to 290° C. and at a total pressure of from 20 to 80 barg (2000 to 8000 kPa), for example 50 to 80 barg (5000 to 8000 kPa).

In some or all embodiments of the present invention, step (a) is carried out a total pressure of from 20 to 80 barg (2000 to 8000 kPa), for example 50 to 80 barg (5000 to 8000 kPa) and the first treatment mixture is a mixture of water vapour and one or more inert gases, for example selected from nitrogen, helium, argon and carbon dioxide, preferably nitrogen and water vapour is present in the first treatment mixture in an amount of 1 to 10 mol %, preferably 4 to 6 mol %.

Suitably, in step (a) the catalyst is contacted with the first treatment mixture for a period of from 10 minutes to 24 hours, for example from 10 minutes to 5 hours, such as 2 to 5 hours, for instance 2 to 3 hours.

In some or all embodiments of the present invention, step (a) is carried out for a period of 10 minutes to 24 hours, such as 2 to 5 hours, for instance 2 to 3 hours at a temperature of from 250° C. to 350° C., such as 260° C. to 300° C., for example from 270° C. to 290° C.

Suitably, the first treatment mixture has a gas hourly space velocity (GHSV) in the range 500 to 40,000 h$^{-1}$, for example 3,000 to 10,000 h$^{-1}$.

The catalyst, after treatment with the first treatment mixture in step (a) of the present invention, is subjected to further treatment by contacting it with a second treatment mixture comprising an inert gas and one or both of dimethyl ether and methanol (step (b)).

Suitably, the second treatment mixture comprises dimethyl ether or methanol in an amount of 1 to 20 mol %, for example 2 to 12 mol %, such as 2 to 10 mol %.

If desired, during step (b) the amount of dimethyl ether and/or methanol present in the second treatment mixture can be adjusted, for example by increasing the amount of dimethyl ether and/or methanol present in the mixture. Suitably, the amounts of each of dimethyl ether and methanol present in the second treatment mixture may be adjusted to be in the range 2 to 12 mol %.

In some or all embodiments of the present invention, methanol is not a component of the second treatment mixture.

In some or all embodiments of the present invention, the inert gas component of the second treatment mixture is selected from nitrogen, helium, argon, carbon dioxide, methane and ethane, preferably nitrogen.

In some or all embodiments of the present invention, the second treatment mixture comprises dimethyl ether and nitrogen as the inert gas component.

In some or all embodiments of the present invention, the second treatment mixture comprises methanol and nitrogen as the inert gas component.

The second treatment mixture may further comprise water vapour. The amount of water vapour present in the second treatment mixture may be the same as or different to the amount of water vapour present in the first treatment mixture. The amount of water vapour in the second treatment mixture can be varied and for carbonylation reaction pressures in the range 50 to 100 barg (500 to 10,000 kPa), is suitably 1 to 10 mol %, for example 4 to 6 mol %.

Suitably, the partial pressure of the water vapour in the second treatment mixture is in the range 0.8 to 8 bar (80 to 800 kPa), for example 1 to 4.8 bar (100 to 480 kPa), preferably 3.2 to 4.8 bar (320 to 480 kPa).

In some or all embodiments of the present invention, the second treatment mixture is a mixture of dimethyl ether, inert gas, for example nitrogen and water vapour. Suitably, in these embodiments, the second treatment mixture comprises dimethyl ether, inert gas and water vapour in an amount 1 to 10 mol %, for example 4 to 6 mol %. More suitably, the second treatment mixture comprises 1 to 20 mol %, for example 2 to 12 mol %, such as 2 to 10 mol % dimethyl ether, inert gas and 1 to 10 mol %, for example 4 to 6 mol % water vapour.

In some or all embodiments of the present invention, the second treatment mixture is a mixture of methanol, inert gas, for example nitrogen and water vapour. Suitably, in these embodiments, the second treatment mixture comprises methanol, inert gas and 1 to 10 mol %, for example 4 to 6 mol % water vapour. More suitably, the second treatment mixture comprises 1 to 20 mol % methanol, inert gas and 1 to 10 mol %, for example 4 to 6 mol % water vapour.

Step (b) may be carried out at the same or at a different temperature to step (a). In some or all embodiments of the present invention, step (b) is carried out at a higher temperature than step (a).

Suitably, step (b) is carried out at a temperature in the range 250° C. to 350° C., for instance 260° C. to 300° C. or 260° C. to 310° C., for example 265° C. to 290° C., such as 270° C. to 290° C.

Step (b) may be carried out at the same or at a different pressure to step (a). Suitably, step (b) is carried out at the carbonylation reaction pressure desired to be used Thus, suitably step (b) is carried out at a total pressure of from 1 to 100 barg (1000 to 10,000 kPa), for example 20 to 80 barg (2000 to 8000 kPa), such as 50 to 80 barg (5000 to 8000 kPa).

Desirably, step (b) is carried out at a temperature of from 250° C. to 350° C., such as 260° C. to 300° C. or 260° C. to 310° C., for example from 265° C. to 290° C. and at a total pressure of from 20 to 80 barg (2000 to 8000 kPa), for example 50 to 80 barg (5000 to 8000 kPa).

In some or all embodiments of the present invention, step (b) is carried out at a temperature of from 250° C. to 350° C., such as 260° C. to 300° C. or 260° C. to 310° C., for example from 265° C. to 290° C. and at a total pressure of from 20 to 80 barg (2000 to 8000 kPa), for example 50 to 80 barg (5000 to 8000 kPa) and the second treatment mixture is a mixture of dimethyl ether, for example in an amount of 1 to 20 mol %, preferably 2 to 12 mol % and an inert gas, for example nitrogen.

In some or all embodiments of the present invention, step (b) is carried out at a temperature of from 250° C. to 350° C., such as 260° C. to 300° C. or 260° C. to 310° C., for example from 265° C. to 290° C. and at a total pressure of from 20 to 80 barg (2000 to 8000 kPa), for example 50 to 80 barg (5000 to 8000 kPa) and the second treatment mixture is a mixture of methanol, for example in an amount of 1 to 20 mol % and an inert gas, for example nitrogen.

Step (a) and step (b) are carried out as sequential steps. Desirably, step (a) and step (b) are carried out in immediate succession. Thus, suitably, step (b) is commenced within a period of 0 to 24 hours after ceasing treatment of the catalyst with the first treatment mixture.

Step (b) may be carried out for a period of at least 10 minutes, for example of from 30 minutes to 100 hours, such as 30 minutes to 72 hours, for instance 30 minutes to 50 hours or for a period of 10 minutes to 1 hour.

Prior to commencing carbonylation step (ii), the catalyst pretreatment step (i) may comprise, in addition to steps (a) and (b), a subsequent step of ceasing the inert gas component of the second treatment mixture (step (c)). Where dimethyl ether is a component of the second treatment mixture, it is desirable that, in step (c), although the inert gas is ceased, the dimethyl ether is continued to provide some or all of the dimethyl ether reactant feed in carbonylation step (ii). Where methanol is a component of the second treatment mixture, the methanol is ceased prior to starting carbonylation step (ii).

Step (c) and carbonylation step (ii) may be carried out concurrently or in immediate succession, that is substantially without interruption. If carried out concurrently, ceasing of inert gas may be carried out gradually in step (c) and carbon monoxide-containing gas is introduced prior to complete cessation of the inert gas.

During treatment of the catalyst in step (b) with a second treatment mixture comprising water vapour, the water vapour need not be present as a component of the second treatment mixture for the entire duration of step (b). In this manner, the water vapour is not present as a feed component to the carbonylation step (ii). Thus, in some or all embodiments of the present invention, the catalyst is pretreated by the steps:

(a) contacting the catalyst with a first treatment mixture comprising water vapour and an inert gas, preferably nitrogen; and (b) contacting the catalyst treated in step (a) with a second treatment mixture comprising an inert gas, preferably nitrogen, water vapour and at least one of dimethyl ether and methanol;

(b') ceasing the water vapour and continuing with the inert gas and the at least one of dimethyl ether and methanol. Suitably, in these embodiments, step (b) may be carried out for a period of at least 1 minute, for example of from 1 minute to 1 hour, such as 1 minute to 30 minutes prior to step (b¹) ceasing the water vapour and, suitably in step (b¹) treatment with dimethyl ether and/or methanol and the inert gas may be continued for a further period of at least 2 hours, for example from 2 hours to 100 hours, such as 5 hours to 72 hours, for instance 5 hours to 50 hours. Suitably, in these embodiments, in step (a) the first treatment mixture is a mixture of water vapour and an inert gas, preferably nitrogen and, preferably in step (b) the inert gas is nitrogen. These embodiments may further comprise a step (c) of ceasing the inert gas prior to starting the carbonylation step (ii).

In some or all embodiments of the present invention, the second treatment mixture does not comprise methanol and in pretreatment step (i) the catalyst is pretreated by the steps:

(a) contacting the catalyst with a first treatment mixture comprising water vapour and an inert gas, preferably nitrogen; and (b) contacting the catalyst treated in step (a) with a second treatment mixture comprising an inert gas, preferably nitrogen and dimethyl ether and water vapour;

($b^i$) ceasing the water vapour and continuing with dimethyl ether and inert gas; and (c) ceasing the inert gas.

In some or all embodiments of the present invention, the second treatment mixture does not comprise dimethyl ether and in pretreatment step (i) the catalyst is pretreated by the steps:

(a) contacting the catalyst with a first treatment mixture comprising water vapour and an inert gas, preferably nitrogen; and (b) contacting the catalyst treated in step (a) with a second treatment mixture comprising an inert gas, preferably nitrogen and methanol and water vapour;

($b^i$) ceasing the water vapour and continuing with methanol and inert gas; and (c) ceasing the inert gas and methanol.

In these embodiments, ceasing of the inert gas and methanol in step (c) may be carried out simultaneously or sequentially, for example wherein methanol is ceased prior to ceasing of the inert gas.

In step (b) of the present invention, the catalyst is contacted with a second treatment mixture of inert gas and one or both of dimethyl ether and methanol, and optionally, and preferably further comprising water vapour, for example for a total period of up to 100 hours. During step (b), it may be desirable, for a short duration, for example a few hours, to discontinue treatment of the catalyst with dimethyl ether and/or methanol and continue treatment of the catalyst with inert gas alone. In instances where water vapour is a component of the second treatment mixture, treatment of the catalyst with water vapour is discontinued preferably prior to ceasing treatment of the catalyst with dimethyl ether. Thus, in some or all embodiments of the present invention, step (b) further comprises, prior to step (c) and subsequent to step ($b^i$), ceasing treatment of the catalyst with the at least one of dimethyl ether and methanol (step ($b^{ii}$)).

Hence, in some or all embodiments of the present invention, the catalyst is pretreated in step (i) by the steps:

(a) contacting the catalyst with a first treatment mixture comprising water vapour and an inert gas, preferably nitrogen; and (b) contacting the catalyst treated in step (a) with a second treatment mixture comprising an inert gas, preferably nitrogen and dimethyl ether and optionally water vapour;

($b^i$) ceasing the optional water vapour;

($b^{ii}$) ceasing the dimethyl ether and continuing with the inert gas; and (c) ceasing the inert gas.

Suitably, in these embodiments, steps (b), ($b^i$) and ($b^{ii}$) are carried out for a total period of 2 to 100 hours during which period, treatment of the catalyst with dimethyl ether is ceased and, if present in the second treatment mixture, treatment of the catalyst with water vapour is also ceased and the catalyst is treated for a time in step ($b^{ii}$) with inert gas alone, after which, treatment of the catalyst with the inert gas is also ceased (step (c)). In these embodiments, step (a) may be carried out for 2 to 5 hours; step (b) may be carried out for 1 minute to 1 hour; step ($b^i$) may be carried out for 5 to 72 hours, for example 9 to 48 hours; and step ($b^{ii}$) may be carried out for a period of 1 to 5 hours, such as 2 to 5 hours. Following step (c), the carbonylation step (ii) may be initiated in-situ by reacting dimethyl ether with a carbon monoxide-containing gas in the presence of the pretreated catalyst to produce a reaction product comprising methyl acetate.

In some or all embodiments of the present invention, the catalyst is pretreated in-situ by a method which comprises steps (a) and (b) and step (c) and optionally one or both of step ($b^i$) and step ($b^{ii}$).

Suitably, the process of the present invention for the carbonylation of dimethyl ether with a carbon monoxide-containing gas in the presence of a zeolite carbonylation catalyst comprises the sequential steps of:

(i) pretreating the catalyst; and (ii) carbonylating dimethyl ether with a carbon monoxide-containing gas in the presence of the catalyst to produce a reaction product comprising methyl acetate; wherein the catalyst pretreatment step (i) comprises the steps:

(a) contacting the catalyst with a first treatment mixture comprising water vapour and preferably an inert gas;

(b) contacting the catalyst treated in step (a) with a second treatment mixture comprising inert gas and dimethyl ether and preferably water vapour; and ($b^i$) optionally ceasing treatment with water vapour; and (c) ceasing the inert gas Preferably, in these embodiments, in step (a) the first treatment mixture comprises an inert gas, preferably nitrogen and in step (b) the second treatment mixture further comprises water vapour and the inert gas is preferably nitrogen and further comprises the above-described step ($b^i$) of ceasing treatment with water vapour and in step (c) dimethyl ether is continued.

Suitably, the process of the present invention for the carbonylation of dimethyl ether with a carbon monoxide-containing gas in the presence of a zeolite carbonylation catalyst comprises the sequential steps of:

(i) pretreating the catalyst; and (ii) carbonylating dimethyl ether with a carbon monoxide-containing gas in the presence of the catalyst to produce a reaction product comprising methyl acetate; wherein the catalyst pretreatment step (i) comprises the steps:

(a) contacting the catalyst with a first treatment mixture comprising water vapour;

(b) contacting the catalyst treated in step (a) with a second treatment mixture comprising inert gas and dimethyl ether and water vapour; and ($b^i$) ceasing the water vapour and continuing with dimethyl ether and inert gas; and (c) ceasing the inert gas.

In step (c), the inert gas is ceased and the dimethyl ether of the second treatment mixture is continued into carbonylation step (ii). Preferably, in step (a), the first treatment mixture further comprises an inert gas.

Suitably, the process of the present invention for the carbonylation of dimethyl ether with a carbon monoxide-containing gas in the presence of a zeolite carbonylation catalyst comprises the sequential steps of:

(i) pretreating the catalyst; and
(ii) carbonylating dimethyl ether with a carbon monoxide-containing gas in the presence of the catalyst to produce a reaction product comprising methyl acetate; wherein the catalyst pretreatment step (i) comprises the steps:
   (a) contacting the catalyst with a first treatment mixture comprising water vapour;
   (b) contacting the catalyst treated in step (a) with a second treatment mixture comprising inert gas, methanol and water vapour; and
   (b$^i$) ceasing the water vapour and continuing with methanol and inert gas; and
   (c) ceasing the inert gas.

Preferably, in step (a), the first treatment mixture further comprises an inert gas. In step (c) the inert gas is ceased prior to carrying out carbonylation step (ii). Methanol may also be ceased in step (c) and prior to carbonylation step (ii). Thus, in step (c), the methanol and inert gas may be ceased simultaneously or sequentially. Suitably, where methanol and inert gas are ceased sequentially in step (c), methanol is ceased prior to the inert gas.

In some or all embodiments of the present invention, catalyst pretreatment step (i) is carried out at a total pressure in the range 1 to 80 barg (100 to 8000 kPa), for example 1 to 70 barg (100 to 7000 kPa), such as 1 to 10 barg (100 to 1000 kPa). Each of the pretreatment steps (a), (b), (b$^i$), (b$^{ii}$) and (c) may be carried out at the same or a different pressure. In these embodiments, catalyst pretreatment step (i) may be carried out at a temperature of from 250° C. to 350° C., such as 260° C. to 310° C., for example from 270° C. to 290° C. Each of the pretreatment steps (a), (b), (b$^i$), (b$^{ii}$) and (c) may be carried out at the same or a different temperature.

In some or all embodiments of the present invention, catalyst pretreatment step (i) is carried out at a lower pressure than the carbonylation step (ii). Each of the pretreatment steps (a), (b), (b$^i$), (b$^{ii}$) and (c) may be carried out at the same or a different pressure wherein each pressure is lower than the carbonylation step (ii). In these embodiments, catalyst pretreatment step (i) may be carried out at a temperature of from 250° C. to 350° C., such as 260° C. to 310° C., for example from 270° C. to 290° C. Each of the pretreatment steps (a), (b), (b$^i$), (b$^{ii}$) and (c) may be carried out at the same or a different temperature.

Each or all of steps (a), (b), (b$^i$), (b$^{ii}$) and (c) in pretreatment step (i) may be carried out at a different pressure and/or a different temperature to the pressure and/or temperature desired to be used in carbonylation step (ii) and thus may be adjusted to the desired temperature and/or pressure prior to commencing step (ii).

The zeolite catalyst to be treated in the present invention may be any crystalline zeolite which is effective to catalyse the carbonylation of dimethyl ether with carbon monoxide to produce acetyls products, particularly methyl acetate.

Zeolites are commercially available in a number of forms, including ammonium and hydrogen forms. Zeolites may also be synthesised using known techniques.

Suitably, zeolites to be treated in accordance with the present invention are in the H-form (hydrogen form). Zeolites in the hydrogen form include those zeolites which possess, typically within the crystal structure, other cations such as ammonium ions, but which zeolites possess predominantly hydrogen ions at the surface and as such are generally considered to be in the hydrogen form.

If desired, the zeolite to be pretreated may be in an ion-exchanged or otherwise metal loaded form with one or more metals, such as copper, silver, nickel, iridium, rhodium, platinum, palladium and cobalt metals and mixtures thereof. Examples include copper mordenites, silver mordenites and copper-silver mordenites.

A large number of zeolite framework types are known in the art, and these are assigned three-letter structure codes by the Structure Commission of the International Zeolite Association, under the authority of IUPAC. *The Atlas of Zeolite Framework Types* (C. Baerlocher, W. M. Meier, D. H. Olson, 5$^{th}$ Ed. Elsevier, Amsterdam, 2001) in conjunction with the web-based version (http://www.iza-structure.org/databases/) is a database of topological and structural details about zeolite frameworks, including the types of ring structures present in zeolites and the dimensions of the channels defined by each ring type.

Zeolites to be pretreated according to the present invention are suitably zeolites which contain at least one channel or pocket (generically referred to throughout this specification as 'channel') which is defined by an 8-member ring.

The window size of the 8-member channel systems of a zeolite suitable for use in processes for the carbonylation of dimethyl ether should be such that the reactant dimethyl ether and carbon monoxide molecules can diffuse freely in and out of the zeolite framework. Suitably, therefore, the window size of the zeolite 8-member ring channel is at least 2.5×3.6 Angstroms.

The zeolite 8-member ring channel may be interconnected with at least one channel defined by a ring with 10 or 12 members.

Examples of zeolites which have at least one channel which is defined by an 8-membered ring and which are suitable for use in processes for the carbonylation of dimethyl ether include zeolites having a framework type selected from MOR, for example mordenite, FER, for example ferrierite or ZSM-35, OFF, for example offretite, and GME, for example gmelinite.

In particular, the zeolite to be pretreated in accordance with the present invention is selected from mordenite, ferrierite and offretite zeolites.

In some or all embodiments of the present invention, the zeolite is mordenite, and, in particular, mordenite in hydrogen form.

The silica to alumina molar ratio of a zeolite to be treated in accordance with the present invention may vary but is suitably at least 5, and preferably less than or equal to 100, for example in the range of from 10 to 30.

Zeolites are commercially available as fine crystalline powders and are typically further modified to enhance their properties for use in catalytic reactions such as by forming the zeolites into shaped particles. Processes for forming zeolites into shaped particles are well-known in the art and may be accomplished by forming a gel or paste of the zeolite powder with the addition of a suitable binder material and then extruding the gel or paste into the desired shape. Zeolite powders may also be formed into shaped particles without the use of a binder.

Desirably therefore, a zeolite to be treated in accordance with the present invention is a zeolite which is composited with a binder material. Suitable binder materials include inorganic oxides such as aluminas, silica-aluminas and silicas.

The particle shape of the zeolite/binder composite is not critical but is suitably in the form of an extrudate, for example extrudates whose cross-sections may be circular or embrace a plurality of arcuate lobes extending outwardly from the central portion of the zeolite particles.

Prior to use in the pretreatment step (i) of the present invention, a zeolite/binder composite may be calcined using any known calcination techniques, such as by heating in air at high temperature, such as at temperatures of 400° C. to 500° C. or higher.

In some or all embodiments of the present invention, the zeolite, preferably mordenite, is composited with a inorganic oxide binder material selected from aluminas, silica-aluminas and silicas, preferably an alumina and the composited zeolite is suitably in the form of an extrudate.

A zeolite pretreated in accordance with the method of present invention is particularly suitable for use as a catalyst in the carbonylation of dimethyl ether with a carbon monoxide-containing gas to produce a carbonylation reaction product comprising methyl acetate. Thus, the present invention yet further provides a pretreated zeolite catalyst having improved catalytic performance for the carbonylation of dimethyl ether with a carbon monoxide-containing gas to produce a reaction product comprising methyl acetate which catalyst is a pretreated catalyst prepared in accordance with any of the methods of pretreatment step (i) of the present invention.

Pretreatment of the zeolite catalyst may be carried out by passing the first and second treatment mixtures through a fixed bed of the catalyst.

In some or all embodiments of the present invention, in step (a) the catalyst is preferably mordenite, the first treatment mixture is a mixture of nitrogen and 1 to 10 mol % water, preferably 4 to 6 mol % water and is carried out, for example at 70 to 80 barg (7000 to 8000 kPa), preferably for a period of 1 to 5 hours, and in step (b) the second treatment mixture is a mixture of nitrogen, 2 to 12 mol % dimethyl ether, for example 2 to 10 mol % dimethyl ether and further comprises water vapour, suitably in an amount of 1 to 10 mol % preferably 4 to 6 mol % and preferably step (b) is commenced after a period of 0 minutes to 24 hours after ceasing treatment of the catalyst with the first treatment mixture.

Contacting a carbon monoxide-containing gas and dimethyl ether in the presence of the pretreated catalyst of the present invention initiates carbonylation of dimethyl ether and produces a reaction product comprising methyl acetate. Any suitable carbonylation reaction conditions may be employed in step (ii) of the present invention.

Suitably, the dimethyl ether feed for step (ii) may be fresh dimethyl ether or may be dimethyl ether present in the second treatment mixture or a mixture thereof.

Suitably, in step (ii) dimethyl ether is present at a concentration of from 1 to 20 mol %, for example 2 to 12 mol %, such as 2 to 10 mol % based on the total gaseous feed to carbonylation step (ii).

The molar ratio of carbon monoxide to dimethyl ether in step (ii) is suitably in the range of from 1:1 to 99:1, such as from 2:1 to 60:1.

Suitably, the partial pressure of carbon monoxide in step (ii) is in the range 1 to 60 barg, for example 10 to 50 barg.

The carbon monoxide-containing gas for use in step (ii) may be pure carbon monoxide or it may be a mixture of carbon monoxide, hydrogen and optionally carbon dioxide, such as a synthesis gas. Suitably, the carbon monoxide-containing gas is a mixture of carbon monoxide and hydrogen.

In mixtures containing carbon monoxide and hydrogen the molar ratio of hydrogen to carbon monoxide is suitably in the range 1 to 12:1, for example 1 to 8:1, such as 1.5 to 4:1. However, if desired other molar ratios may also be used.

As water can inhibit the carbonylation of dimethyl ether with a carbon monoxide-containing gas to produce a carbonylation reaction product comprising methyl acetate, carbonylation step (ii) is desirably carried out under anhydrous conditions. Desirably, the total amount of water present in the feed components to carbonylation step (ii) is less than 1 mol %, for example less than 0.5 mol %, such as less than 0.1 mol %.

Suitably, prior to use in step (ii) the carbon monoxide-containing gas and dimethyl ether are dried such that the amount of water fed to step (ii) is less than 1 mol %, and preferably less than 0.1 mol % based on the total gaseous feed to step (ii).

In step (ii) carbonylation is suitably carried out at a temperature in the range 250 to 350° C., for example in the range 270 to 300° C.

In step (ii) carbonylation is suitably carried out at a total pressure in the range 1 to 100 barg (1000 to 10,000 kPa), for example 20 to 80 barg (2000 to 8000 kPa).

In some or all embodiments of the present invention, step (ii) is conducted at a temperature in the range 250° C. to 350° C., for example 270° C. to 300° C. and at a total pressure in the range of from 1 to 100 barg (1000 to 10,000 kPa), such as 20 to 80 barg (2000 to 8000 kPa).

In some or all embodiments of the present invention, step (ii) is conducted at a temperature of 250° C. to 350° C., for example 270° C. to 300° C. or 270° C. to 310° C., a pressure in the range 50 to 100 barg (5000 to 10,000 kPa), for example 50 to 80 barg (5000 to 8000 kPa), dimethyl ether is present at a concentration in the range 2 to 12 mol %, such as 2 to 10 mol % and the carbon monoxide-containing gas is a synthesis gas having a hydrogen to carbon monoxide molar ratio in the range 1 to 12:1, for example 1 to 8:1, such as 1.5 to 4:1.

In step (ii), the carbonylation reaction is suitably carried out at a total gas hourly space velocity (GHSV) in the range of from 500 to 40,000 h$^{-1}$, for example 3,000 to 10,000 h$^{-1}$.

Suitably, step (ii) is carried out as a vapour phase process, for example as a fixed bed or fluidised bed process. Thus, step (ii) may be carried out by passing a gaseous feed of dimethyl ether and carbon monoxide and optionally hydrogen, through a fixed bed or fluidised bed of the pretreated catalyst maintained at the desired carbonylation reaction temperature. Preferably, step (ii) is carried out by passing a gaseous feed of dimethyl ether and synthesis gas through a fixed bed of the pretreated catalyst maintained at the desired carbonylation reaction temperature.

The reaction product of step (ii) comprises methyl acetate. Typically, the reaction product comprises mainly methyl acetate with lesser amounts of acetic acid. The reaction product may further comprise additional components such as one or more of unreacted dimethyl ether, unreacted carbon monoxide and hydrogen.

Desirably, methyl acetate, is recovered from the reaction product of step (ii) and some or all of the recovered methyl acetate is converted to acetic acid, for example by a hydrolysis process.

The reaction product of step (ii) is typically in gaseous form. Suitably, the reaction product is cooled and separated to recover a methyl acetate-rich liquid stream and a gas stream comprising, for example unreacted carbon monoxide and hydrogen. Cooling of the reaction product may be carried out using one or more heat exchange means, such as conventional heat exchangers, to cool the reaction product to, for example a temperature of 50° C. or less. A methyl acetate-rich liquid stream may be recovered from the gas stream, for example in one or more gas/liquid separation means such as a knock-out drum or a tangential inlet drum.

Typically, the methyl acetate-rich liquid stream comprises mainly methyl acetate and may also comprise minor amounts of one or more of unreacted dimethyl ether, water and dissolved inert gases. Methyl acetate may be recovered from the methyl acetate-rich liquid stream, for example by distillation, and the recovered methyl acetate sold as such or used as a feedstock in downstream chemical processes. Suitably some or all of the recovered methyl acetate may be converted to acetic acid, preferably by a hydrolysis process. Hydrolysis of the recovered methyl acetate may be carried out using any known processes, such as catalytic distillation processes. Typically, in catalytic distillation processes for the hydrolysis of methyl acetate, methyl acetate is hydrolysed with water in a fixed-bed reactor employing an acidic catalyst, such as an acidic ion exchange resin or a zeolite, to produce a mixture comprising acetic acid and methanol from which acetic acid, and methanol may be separated by distillation, in one or more distillation stages.

The present invention will now be illustrated with reference to the following non-limiting examples.

EXAMPLES

General Apparatus I

Catalyst pretreatments and carbonylation reactions were conducted in a plug-flow reactor having an internal diameter of 24 mm and capable of operation at up to 350° C. and 80 barg (8000 kPa) pressure. The reactor was equipped with four independent gas feeds controlled by independent mass-flow controllers, two independent liquid feeds to an in-line vapouriser, and two on-line gas chromatographs for periodic analysis of the reactor effluent stream. The reactor was mounted vertically and packed with an inert supporting bed of 12.5 mL silicon carbide (F20, 0.85 to 1.18 mm), a catalyst bed containing 50 mL of 3.2 mm extrudates of H-mordenite composited with 20% gamma-alumina and diluted with 120 mL silicon carbide (F10, 2.0 to 2.36 mm), and an inert top layer of 40 mL silicon carbide (F14, 1.18 to 1.7 mm).

Space time yield (STY) of a carbonylation reaction was calculated as acetic acid equivalents per dm3 of catalyst per hour. Acetic acid equivalents were determined by multiplication of the STY for methyl acetate production by 0.81 (i.e the molecular weight of acetic acid/molecular weight of methyl acetate)

Experiment A

This Experiment demonstrates the use of a catalyst pretreated solely with water vapour in a process for the carbonylation of dimethyl ether with a carbon monoxide containing gas and is not an example according to the invention.

This Experiment was carried out using apparatus I described above. The reactor, containing the catalyst, was heated to a temperature of 270° C. and, a pressure of 70 barg (7000 kPa). The catalyst was contacted, at this temperature and pressure, with a mixture of 5 mol % water vapour and a synthesis gas ($H_2$:CO molar ratio of 4:1) for a period of 4.5 hours. At the end of this 4.5 hour period, the composition of the mixture was changed to 5 mol % dimethyl ether, 5 mol % water vapour and synthesis gas and the catalyst was contacted with this mixture for a period of 30 minutes. At the end of this 30 minute period, the supply of water vapour was ceased and contact of the catalyst with the mixture of dimethyl ether and synthesis gas continued; a prompt transient 15K exotherm was observed at this point. After 100 hours on stream the STY of the carbonylation reaction of dimethyl ether with carbon monoxide was determined to be 208 g/dm$^3$/h. During the next 72 hours, the temperature was gradually increased from 270° C. to 300° C. and the syngas composition adjusted to a $H_2$:CO molar ratio of 2:1.250 hours after the introduction of dimethyl ether into the reactor, the STY was found to be 428 g/dm$^3$/h and the molar selectivity to methyl acetate and acetic acid was 93.8%.

Example 1

This Example 1 was carried out using apparatus I described above. The reactor containing the catalyst was heated to a temperature of 270° C. and a pressure of 70 barg (7000 kPa). The catalyst was contacted, at this temperature and pressure, with a mixture of 5 mol % water vapour and nitrogen for a period of 4.5 hours. At the end of this 4.5 hour period, the catalyst was contacted with a mixture of 5 mol % dimethyl ether, 5 mol % water vapour and nitrogen for a period of 30 minutes. At the end of this 30 minute period, the water vapour was ceased and contact of the catalyst with the mixture of dimethyl ether and nitrogen continued; a prompt transient 8K exotherm was observed at this point. The catalyst was contacted with this mixture of dimethyl ether and nitrogen for a further period of 15 hours. At the end of this 15 hour period, the nitrogen feed was ceased and the dimethyl ether feed continued. Carbonylation of the dimethyl ether feed was started in the presence of the catalyst by introducing a synthesis gas feed ($H_2$:CO molar ratio of 4:1) into the reactor. After 100 hours on stream the STY was determined to be 253 g/dm$^3$/h. During the next 72 hours, the temperature was gradually increased from 270° C. to 300° C. and the syngas composition was adjusted to $H_2$:CO molar ratio of 2:1.250 hours after the introduction of dimethyl ether the STY was found to be 479 g/dm$^3$/h and the molar selectivity to methyl acetate and acetic acid was 96.2%.

The results of this Example demonstrate that catalysts pretreated in accordance with the present invention show greater activity and improved selectivity for carbonylation reactions compared to the catalyst used in Experiment A which had not been treated in accordance with the present invention.

Example 2

This Example 2 was carried out using apparatus I described above. The reactor containing the catalyst was heated to a temperature of 290° C. and a pressure of 70 barg (7000 kPa). The catalyst was contacted, at this temperature and pressure, with a mixture of 5 mol % water vapour and nitrogen for a period of 4.5 hours. At the end of this 4.5 hour period, the catalyst was contacted with a mixture of 5 mol % dimethyl ether, 5 mol % water vapour and nitrogen for a period of 30 minutes. At the end of this 30 minute period, the water vapour was ceased and the amount of dimethyl ether in the mixture was increased to 9 mol %. The catalyst was contacted with this dimethyl ether/nitrogen mixture for a further period of 71.5 hours at 290° C. At the end of this period, the reactor temperature was reduced from 290° C. to 260° C., the nitrogen feed was stopped and the dimethyl ether feed continued. Carbonylation of the dimethyl ether was started by introducing a synthesis gas feed ($H_2$:CO molar ratio of 2:1) into the reactor in the presence of the catalyst. During the first 100 hours of reaction the temperature was increased from 260° C. to 275° C. and from 275° C. to 285° C. then reduced to 284° C. After 328 hours on stream the STY was determined to be 742 g/dm$^3$/h and the molar selectivity to methyl acetate and acetic acid was 98.2%.

The results of this Example demonstrate that catalysts pretreated in accordance with the present invention show greater activity and improved selectivity for carbonylation reactions compared to the catalyst used in Experiment A which had not been treated in accordance with the present invention.

Example 3

This Example 3 was carried out using apparatus I described above. The reactor containing the catalyst was heated to a temperature of 290° C. and a pressure of 70 barg (7000 k Pa). The catalyst was contacted at this temperature and pressure with a mixture of 5 mol % water vapour and nitrogen for a period of 4.5 hours. At the end of this 4.5 hour period, the catalyst was contacted with a mixture of 5 mol % methanol, 5 mol % water vapour and nitrogen for a period of 30 minutes. At the end of this 30 minute period, the water vapour supply was stopped; the amount of methanol in the methanol and nitrogen mixture was increased to 9 mol % and the catalyst contacted with this mixture for a further period of 71.5 hours, after which time it was ceased and the temperature reduced from 290° C. to 260° C. At 260° C., 9 mol % dimethyl ether was introduced and the carbonylation reaction started by introducing a synthesis gas feed ($H_2$:CO molar ratio of 2:1) into the reactor in the presence of the catalyst. During the first 100 hours of the reaction the temperature was increased from 260° C. to 275° C. and then from 275° C. to 285° C. and then reduced to 284° C. After 328 hours on stream the STY was determined to be 701 g/dm$^3$/h and the molar selectivity to methyl acetate and acetic acid was 97.8%.

The results of this Example demonstrate that catalysts pretreated in accordance with the present invention show greater activity and improved selectivity for carbonylation reactions compared to the catalyst used in Experiment A which had not been treated in accordance with the present invention.

General Apparatus II

Catalyst pretreatment and carbonylation reactions were carried out in a multi-channel unit having 16 reactors, each reactor having an internal diameter of 9.2 mm and an independent temperature control. Each reactor contained 3 ml of a commercially available H-mordenite catalyst composited with 20% gamma alumina having a particle size in the range 1.4-1.7 mm and diluted with 3.0 ml of corundum of particle size of 125-160 microns. Reactor effluent streams were periodically analysed by on-line gas chromatography. Space time yield (STY) of a carbonylation reaction was calculated as acetic acid equivalents per dm3 of catalyst per hour. Acetic acid equivalents were determined by multiplication of the STY for methyl acetate production by 0.81 (i.e the molecular weight of acetic acid/molecular weight of methyl acetate)

Example 4

This Example 4 was carried out using apparatus II described above. The reactor containing the catalyst was heated to a temperature of 275° C. and a pressure of 70 barg (7000 kPa). The catalyst was contacted, at this temperature and pressure, with a mixture of nitrogen and 5 mol % water vapour for a period of 2.5 hours. At the end of this 2.5 hour period, the reactor temperature was reduced from 275° C. to 265° C. and the catalyst was contacted with a mixture of 2 mol % dimethyl ether, nitrogen and 5 mol % water vapour for a period of 30 minutes. At the end of this 30 minute period, the supply of water vapour was discontinued and the catalyst contacted with the 2 mol % dimethyl-ether and nitrogen mixture for a further 1.5 hours before the concentration of dimethyl ether in the dimethyl ether/nitrogen mixture was increased to 10 mol %. 48 hours after termination of the water vapour, the nitrogen feed was discontinued, the reactor temperature was increased from 275° C. to 280° C. and carbonylation of the dimethyl ether was started by introducing a synthesis gas having a $H_2$:CO molar ratio of 4:1 into the reactor in the presence of the catalyst. After 100 hours on stream the STY was determined to be 510 g/dm$^3$/h.

Example 5

This Example 5 was carried out using apparatus II described above. The reactor containing the catalyst was heated to a temperature of 275° C. and a pressure of 70 barg (7000 kPa). The catalyst was contacted for 2.5 hours at this temperature and pressure with a mixture of nitrogen and 5 mol % water vapour. After this 2.5 hour period the catalyst was contacted with a mixture of 2 mol % dimethyl ether, nitrogen and 5 mol % water vapour for a period of 30 minutes. At the end of this 30 minute period, the water vapour feed was discontinued and the catalyst was contacted with the 2 mol % dimethyl ether and nitrogen mixture for a further 1.5 hours before the concentration of dimethyl ether in the mixture was increased to 10 mol %. 48 hours after termination of the water vapour, the nitrogen feed was ceased, the reactor temperature was increased from 275° C. to 280° C. and carbonylation of the dimethyl ether was started by introducing a synthesis gas having a $H_2$:CO molar ratio of 4:1 into the reactor in the presence of the catalyst. After 100 hours on stream the STY was determined to be 520 g/dm$^3$/h.

Example 6

This Example 6 was carried out using apparatus II described above. The reactor containing the catalyst was heated to a temperature of 275° C. and a pressure of 70 barg (7000 kPa). The catalyst was contacted for 2.5 hours at this temperature and pressure with a mixture of nitrogen and 5 mol % water vapour. At the end of this 2.5 hour period, the temperature was increased from 275° C. to 290° C. and the catalyst was contacted with a mixture of 2 mol % dimethyl ether, nitrogen and 5 mol % water vapour for a period of 30 minutes. At the end of this 30 minute period, the water vapour feed was terminated and the catalyst was contacted with the 2 mol % dimethyl ether and nitrogen mixture for a further 1.5 hours before the concentration of dimethyl ether in the mixture was increased to 10 mol %. 48 hours after termination of the water vapour, the nitrogen was ceased, the reactor temperature was reduced to 280° C. and carbonylation of the dimethyl ether was started by introducing a synthesis gas having a $H_2$:CO molar ratio of 4:1 into the reactor in the presence of the catalyst. After 100 hours on stream the STY was determined to be 600 g/dm$^3$/h.

Example 7

This Example 7 was carried out using apparatus II described above. The reactor containing the catalyst was heated to a temperature of 275° C. and a pressure of 70 barg (7000 kPa). The catalyst was contacted for 2.5 hours at this temperature and pressure with a mixture of nitrogen and 5 mol % water vapour, After this 2.5 hour period, the temperature was increased from 275° C. to 290° C. and the catalyst was contacted with a mixture of 2 mol % dimethyl ether, 5 mol % water vapour and nitrogen for a period of 30 minutes. At the end of this 30 minute period, the supply of water vapour was discontinued and the catalyst was contacted with the nitrogen and 2 mol % dimethyl ether mixture for a period of 1.5 hours before the concentration of dimethyl ether in the mixture was increased to 10 mol %. 70 hours after termination of the water vapour, the nitrogen feed was discontinued, the reactor temperature was reduced to 280° C. and carbonylation of the dimethyl ether started by introducing a synthesis gas having a $H_2$:CO molar ratio of 4:1 into the reactor in the presence of the catalyst. After 100 hours on stream the STY was determined to be 710 g/dm³/h.

Example 8

This Example 8 was carried out using apparatus II described above. The reactor containing the catalyst was heated to a temperature of 275° C. and a pressure of 70 barg (7000 kPa). The catalyst was contacted for 2.5 hours at this temperature and pressure with a mixture of nitrogen and 5 mol % water vapour. After this 2.5 hour period, the catalyst was contacted with a mixture of nitrogen, 2 mol % dimethyl ether and 5 mol % water vapour for a period of 30 minutes. At the end of this 30 minute period, the water vapour was discontinued and contact of the catalyst continued with 2 mol % dimethyl ether and nitrogen mixture for a further 1.5 hours before the concentration of dimethyl ether in the mixture was increased to 10 mol %. After contacting the catalyst with this 10 mol % dimethyl ether/nitrogen mixture for a period of 8 hours, the dimethyl ether feed was ceased and the catalyst was contacted solely with nitrogen for a period of 2 hours. At the end of this 2 hour period, the nitrogen was ceased and the reactor temperature was increased from 275° C. to 280° C. The carbonylation reaction was started by introducing dimethyl ether and a synthesis gas having a $H_2$:CO molar ratio of 4:1 into the reactor in the presence of the catalyst. After 100 hours on stream the STY was determined to be 520 g/dm³/h.

Example 9

This Example 9 was carried out using apparatus II described above. The reactor containing the catalyst was heated to a temperature of 275° C. and a pressure of 70 barg (7000 kPa). The catalyst was contacted for 2.5 hours at this temperature and pressure with a mixture of nitrogen and 5 mol % water vapour. After this 2.5 hour period, the catalyst was contacted with a mixture of nitrogen, 2 mol % dimethyl ether and 5 mol % water vapour for a period of 30 minutes. At the end of this 30 minute period, the water vapour was discontinued and contact of the catalyst was continued with the 2 mol % dimethyl ether and nitrogen mixture for a further 1.5 hours before the concentration of dimethyl ether in the dimethyl ether/nitrogen mixture was increased to 10 mol %. After contacting the catalyst with the 10 mol % dimethyl ether/nitrogen mixture for 46 hours, the dimethyl ether feed was ceased and the catalyst contacted solely with nitrogen for a period of 2 hours. At the end of this 2 hour period, the nitrogen was ceased, the reactor temperature was increased from 275° C. to 280° C. The carbonylation reaction was started by introducing dimethyl ether and a synthesis gas having a $H_2$:CO molar ratio of 4:1 into the reactor in the presence of the catalyst. After 100 hours on stream the STY was determined to be 540 g/dm³/h.

The invention claimed is:

1. A process for the carbonylation of dimethyl ether with a carbon monoxide-containing gas in the presence of a zeolite carbonylation catalyst which process comprises the sequential steps of:
   (i) pretreating the catalyst; and
   (ii) carbonylating the dimethyl ether with the carbon monoxide-containing gas to produce a reaction product comprising methyl acetate;
   wherein the pretreatment of the catalyst in step (i) comprises the steps:
   (a) contacting the catalyst with a first treatment mixture comprising water vapour;
   (b) contacting the catalyst treated in step (a) with a second treatment mixture comprising an inert gas and at least one of dimethyl ether and methanol; and
   (c) ceasing the inert gas component of the second treatment mixture.

2. A process according to claim 1 wherein the first treatment mixture is a mixture of water vapour and one or more inert gases.

3. A process according to claim 1 wherein the second treatment mixture further comprises water vapour.

4. A process according to claim 2 wherein the second treatment mixture comprises water vapour at a partial pressure in the range 0.8 to 8 bar (80 to 800 kPa).

5. A process according to claim 3 wherein the process further comprises during step (b), a step (b') ceasing the water vapour and continuing treatment with the inert gas and the at least one of dimethyl ether and methanol.

6. A process according to claim 5 wherein step (b) is carried out for a period of 1 minute to 1 hour prior to step (b').

7. A process according to claim 5 wherein prior to step (c) the at least one of dimethyl ether and methanol is discontinued.

8. A process according to claim 1 wherein the second treatment mixture comprises dimethyl ether in an amount of 1 to 20 mol %.

9. A process according to claim 1 wherein each of steps (a) and (b) is carried out at a temperature in the range 250° C. to 350° C.

10. A process according to claim 1 wherein the zeolite has at least one channel which is defined by an 8-membered ring.

11. A process according to claim 10 wherein the zeolite has a framework type selected from MOR, FER, OFF and GME.

12. A process according to claim 10 wherein the zeolite is mordenite.

13. A process according to claim 1 wherein the zeolite is composited with a binder material.

14. A process according to claim 12 wherein the binder material is an inorganic oxide selected from aluminas, silica-aluminas and silicas.

15. A process according to claim 1 wherein the carbon monoxide-containing gas is a mixture of hydrogen and carbon monoxide.

16. A process according to claim 15 wherein hydrogen and carbon monoxide are present in the mixture in a hydrogen to carbon monoxide molar ratio in the range 1 to 12:1.

17. A process according to claim 1 wherein the carbonylation step (ii) is carried out at a temperature in the range 250° C. to 350° C.

18. A process according to claim 1 wherein methyl acetate is recovered from the reaction product of step (ii) and some or all of the recovered methyl acetate is converted to acetic acid.

\* \* \* \* \*